(12) United States Patent
Kim

(10) Patent No.: US 11,773,575 B2
(45) Date of Patent: Oct. 3, 2023

(54) DRAINAGE NET FOR SUPPRESSING BIOFILM FORMATION

(71) Applicant: Young Wook Kim, Seoul (KR)

(72) Inventor: Young Wook Kim, Seoul (KR)

( * ) Notice: Subject to any disclaimer, the term of this patent is extended or adjusted under 35 U.S.C. 154(b) by 0 days.

(21) Appl. No.: 17/773,620

(22) PCT Filed: Oct. 8, 2020

(86) PCT No.: PCT/KR2020/013809
§ 371 (c)(1),
(2) Date: May 2, 2022

(87) PCT Pub. No.: WO2021/096069
PCT Pub. Date: May 20, 2021

(65) Prior Publication Data
US 2022/0372741 A1    Nov. 24, 2022

(30) Foreign Application Priority Data

Nov. 13, 2019  (KR) .......................... 10-2019-0145003

(51) Int. Cl.
*E03C 1/264* (2006.01)
*A61L 2/03* (2006.01)

(52) U.S. Cl.
CPC ................ *E03C 1/264* (2013.01); *A61L 2/03* (2013.01)

(58) Field of Classification Search
CPC .............. E03C 1/264; E03C 1/26; A61L 2/03
USPC ........................................................... 4/652
See application file for complete search history.

(56) References Cited

U.S. PATENT DOCUMENTS

| 157,957 | A | * | 12/1874 | Atwater | .................. | E03C 1/264 |
| | | | | | | 4/291 |
| 243,648 | A | * | 6/1881 | Stimpson | ................ | E03C 1/264 |
| | | | | | | 4/291 |
| 287,246 | A | * | 10/1883 | Coomber | ................ | E03C 1/264 |
| | | | | | | 4/291 |
| 769,001 | A | * | 8/1904 | Lawrence | ............... | E03C 1/264 |
| | | | | | | 4/291 |

(Continued)

FOREIGN PATENT DOCUMENTS

| CN | 102197000 A | 9/2011 |
| CN | 216337991 U | 4/2022 |
| DE | 20200500505 U1 | 4/2005 |
| JP | 06-046069 U | 6/1994 |

(Continued)

OTHER PUBLICATIONS

A Chinese Office Action dated Jul. 3, 2023 issued in Chinese Patent Application No. 2023070301322880.

*Primary Examiner* — Erin Deery
(74) *Attorney, Agent, or Firm* — INVENSTONE Patent, LLC

(57) ABSTRACT

The present invention provides a drainage net for suppressing biofilm formation, the drainage net including a drainage net main body having a cylindrical structure opened at an upper side thereof and having drainage holes, a first electrode disposed outside or inside the main body, a second electrode grounded, spaced apart from the first electrode at a predetermined interval, and disposed outside or inside the main body, and a voltage supply unit configured to apply, to the first electrode, at least one of an alternating current (AC) voltage, a direct current (DC) voltage, and a voltage in which the AC voltage and the DC voltage are superimposed.

13 Claims, 15 Drawing Sheets

(56) References Cited

U.S. PATENT DOCUMENTS

| | | | | |
|---|---|---|---|---|
| 852,044 | A * | 4/1907 | Van Der Minden | E03C 1/264 |
| | | | | 4/291 |
| 1,996,279 | A * | 4/1935 | Dillon | E03C 1/264 |
| | | | | D23/209 |
| 3,933,606 | A | 1/1976 | Harms | |
| 3,985,994 | A * | 10/1976 | Eloranta | E03C 1/22 |
| | | | | 219/535 |
| 6,491,814 | B1 * | 12/2002 | Wheeler | E03C 1/264 |
| | | | | 4/294 |
| 7,150,576 | B1 * | 12/2006 | Kambeyanda | E03C 1/282 |
| | | | | 401/292 |
| 2012/0012510 | A1 * | 1/2012 | Ventura | E03C 1/264 |
| | | | | 210/163 |
| 2013/0185857 | A1 * | 7/2013 | Worth | E03C 1/264 |
| | | | | 4/294 |
| 2016/0040410 | A1 * | 2/2016 | Carpenter-Crawford | |
| | | | | E03C 1/18 |
| | | | | 4/652 |
| 2017/0057846 | A1 * | 3/2017 | Zereshkian | A61L 2/035 |

FOREIGN PATENT DOCUMENTS

| | | |
|---|---|---|
| JP | 2010-263962 A | 11/2010 |
| JP | 2014-008177 A | 1/2014 |
| KR | 10-2007-0098293 A | 10/2007 |
| KR | 10-2008-0056284 A | 6/2008 |
| KR | 10-2010-0088727 A | 8/2010 |
| KR | 10-2017-0107642 A | 9/2017 |
| KR | 10-1812008 B1 | 12/2017 |
| KR | 10-2019-0105697 A | 9/2019 |
| WO | 2007/044609 A1 | 4/2007 |
| WO | 2016/080620 A1 | 5/2016 |

\* cited by examiner

DRAINAGE NET FOR SUPPRESSING BIOFILM FORMATION

CROSS-REFERENCE TO RELATED APPLICATIONS

This application is a National Stage filing under 35 U.S.C. 371 of International Application No. PCT/KR2020/013809, filed on Oct. 8, 2020, which claims the benefit of earlier filing date and right of priority to Korean Application No. 10-2019-0145003, filed on Nov. 13, 2019, in the Korean Intellectual Property Office, the contents of which are all hereby incorporated by reference herein in their entirety.

BACKGROUND OF THE DISCLOSURE

Technical Field

The present invention relates to a drainage net for suppressing biofilm formation and a method of manufacturing the same, and more particularly, to a drainage net for suppressing biofilm formation, which is configured to suppress biofilm formation by applying an electric field.

Background Art

In general, a sink is installed in a kitchen in a house or restaurant and provides a space for washing kitchen containers such as various types of dishes. The sink is configured to be supplied with washing water and discharge the washing water, which has been used to wash the kitchen container, to the outside.

Meanwhile, in a general structure of a drainage port installed in the sink, the drainage port is provided at a lower side of a center of a bottom surface of the sink, and a drainage net capable of filtering out leftover food is fixedly inserted into the drainage port. A drainage hose is connected to the drainage port and disposed below the drainage net so that the used washing water may be discharged. In this case, a cover may be disposed above the drainage net.

With this structural feature, when washing water and leftover food flow into the drainage port, the drainage net filters out leftover food, and only the washing water may be discharged through the drainage hose.

In this case, the drainage net serves to filter out the leftover food while preventing the leftover food from being discharged through the drainage port. The drainage net may be mainly made of plastic or stainless.

However, the drainage net is always wet and filled with leftover food, which causes a problem in that the propagation of bacteria forms a biofilm and produces severe offensive odor.

Meanwhile, as a method of suppressing biofilm formation in the drainage net, there is a method that applies a cleaning agent or chlorine bleach onto the drainage net to prevent the propagation of bacteria inside and outside the drainage net and kill the bacteria. However, the above-mentioned method consumes a large amount of chlorine bleach, which causes a problem of environmental pollution.

Accordingly, there is a consistent need to develop a new system capable of reducing environmental pollution and more effectively suppressing biofilm formation in the drainage net.

The Background Art is provided to make it easy to understand the present invention. It should not be interpreted that the contents disclosed in the Background Art are present in prior arts.

SUMMARY OF THE DISCLOSURE

Meanwhile, regarding a solution for solving the above-mentioned problem with the system for suppressing biofilm formation in the drainage net in the related art, the inventors of the present invention could recognize a method of reducing concentration of a chemical agent such as a cleaning agent or chlorine bleach by mitigating a structure of a microorganism film by applying an electric field to a structure of a drainage net.

The inventors of the present invention intended to develop the system for suppressing biofilm formation in the drainage net, the system being configured to reduce the risk of electric shock while effectively suppressing biofilm formation.

As a result, the inventors of the present invention could develop the system for suppressing biofilm formation, which is capable of adjusting intensity of the electric field.

More specifically, the inventors of the present invention could recognize that the electric field was more safely applied, and the biofilm was also effectively removed when an alternating current (AC) voltage and a direct current (DC) voltage were independently applied or when a voltage in which the AC voltage and the DC voltage were superimposed were applied.

In this case, the inventors of the present invention could apply the system for suppressing biofilm formation to the structure of the drainage net as a solution for effectively suppressing biofilm formation.

In particular, the inventors of the present invention intended to apply an electrode capable of supplying the two types of voltages to the structure of the drainage net. Therefore, it could be expected that the biofilm formation in the sink could be suppressed without spatial or temporal restriction.

Moreover, the inventors of the present invention could recognize that the provision of the structure of the drainage net capable of suppressing biofilm formation could solve the problem of environmental pollution caused by the use of a chemical agent.

Meanwhile, the inventors of the present invention could recognize structures and arrangements of electrodes in the structure of the drainage net capable of supplying the electric field with high efficiency to the structure of the drainage net, i.e., increasing electric field density.

Therefore, an object of the present invention is to provide a drainage net for suppressing biofilm formation, in which first and second electrodes having various structures are arranged on a drainage port main body, and a voltage supply unit is provided to apply an AC voltage, a DC voltage, or a voltage in which the AC voltage and the DC voltage are superimposed.

Another object of the present invention is to provide an insertable device for suppressing biofilm formation, which includes a first electrode and a second electrode grounded and spaced apart from the first electrode at a predetermined interval, in which the first electrode and the second electrodes form a pattern to surround a part of a lateral side of a drainage net.

Technical problems of the present invention are not limited to the aforementioned technical problems, and other technical problems, which are not mentioned above, may be clearly understood by those skilled in the art from the following descriptions.

To achieve the above-mentioned objects, an embodiment of the present invention provides a drainage net for suppressing biofilm formation. In this case, the drainage net may include: a drainage net main body having a cylindrical structure opened at an upper side thereof and having drainage holes; a first electrode disposed outside or inside the main body; a second electrode grounded, spaced apart from the first electrode at a predetermined interval, and disposed outside or inside the main body; and a voltage supply unit configured to apply, to the first electrode, at least one of an alternating current (AC) voltage, a direct current (DC) voltage, and a voltage in which the AC voltage and the DC voltage are superimposed.

According to the feature of the present invention, the main body may include: an annular rim portion; and a plurality of columns disposed along the rim portion and provided inside or outside the rim portion. In this case, the plurality of columns may be each opened at an upper or lower side thereof, and the drainage holes may be formed between the plurality of columns. In addition, the first electrode may include: a first insertion electrode insertable into the opened upper or lower side; and an annular electrode disposed one side of the first insertion electrode and corresponding to the rim portion. Further, the second electrode may include: a second insertion electrode insertable into the remaining opened upper or lower side; and a base electrode disposed at the lower side when the second insertion electrode is inserted into the remaining opened upper or lower side and including a plurality of circular electrodes having different diameters and disposed to be spaced apart from one another.

According to the feature of the present invention, the columns each opened only at the upper side thereof among the plurality of columns and the columns each opened only at the lower side thereof among the plurality of columns may be alternately arranged inside or outside the rim portion of the main body.

According to another feature of the present invention, the first electrode may further include: a support electrode disposed in parallel with the first insertion electrode; and a bottom electrode perpendicularly connected to one end of the support electrode and spaced apart from the base electrode of the second electrode at a predetermined interval when the first insertion electrode is inserted into the opened upper or lower side.

According to still another feature of the present invention, the main body may further include a bottom portion having a plurality of drainage holes, the bottom portion being fixed to or seated on the lower side of the main body.

According to another feature of the present invention, the first electrode may be disposed at a portion inside or outside the main body. In addition, the second electrode may be disposed at the remaining portion inside or outside the main body.

According to another feature of the present invention, the first insertion electrode may be provided in plural, and the second insertion electrode may be provided in plural. In this case, at least one of the plurality of first insertion electrodes and at least one of the plurality of second insertion electrode are insertable into the opened upper or lower sides, respectively.

According to another feature of the present invention, at least one of the AC voltage, the DC voltage, and the voltage in which the AC voltage and the DC voltage are superimposed, which is 0.25 to 5 V, may be applied to a surface of the drainage net.

According to another feature of the present invention, the predetermined interval may be 0.01 to 50 mm, and a diameter of the first or second electrode may be 0.01 to 20 mm.

To achieve the above-mentioned objects, another embodiment of the present invention provides a drainage net for suppressing biofilm formation. In this case, the drainage net according to another embodiment of the present invention may include: a main body having a cylindrical structure having lateral and lower sides; a plurality of first electrodes disposed on the lateral and lower sides and provided in a direction parallel to the lower side; a second electrode grounded, spaced apart from the plurality of first electrodes, disposed on the lateral and lower sides, and provided in the direction parallel to the lower side; and a voltage supply unit configured to supply a voltage to the first electrode.

According to the feature of the present invention, the first electrode may include: a plurality of first circular electrodes disposed in a row at the lateral side and having the same diameter; and a plurality of second circular electrodes disposed at the lower side and having different diameters. In addition, the second electrode may include: a plurality of third circular electrodes disposed in a row at the lateral side and having the same diameter; and a plurality of fourth circular electrodes disposed at the lower side and having different diameters. Further, the first and third circular electrodes may be alternately arranged at the lateral side of the main body, and the second and fourth circular electrodes may be alternately arranged at the lower side of the main body.

To achieve the above-mentioned objects, still another embodiment of the present invention provides an insertable device for suppressing biofilm formation. In this case, the insertable device may include: a first electrode configured to define a lattice pattern configured to surround a part of a lateral side of a drainage net having a cylindrical structure; a second electrode grounded, spaced apart from the first electrode, and configured to define the lattice pattern together with the first electrode to surround a part of the lateral side of the drainage net; and a voltage supply unit configured to supply a voltage to the first electrode.

According to the feature of the present invention, the insertable device may further include an insulating layer configured to surround at least a part of the first or second electrode, and the insulating layer is made of at least one of $Al_2O_3$, $SiO_2$, $Si_3N_4$, silicone, Teflon, and plastic.

According to the present invention, it is possible to solve the problem with the system for suppressing biofilm formation in the related art that causes environmental issue because the system uses a strong chemical agent such as chlorine bleach to suppress the proliferation of bacteria and biofilm formation.

More specifically, the present invention provides the drainage net for suppressing biofilm formation, which is configured to apply the AC voltage, the DC voltage, or the voltage in which the AC voltage and the DC voltage are superimposed. Therefore, it is possible to more safely apply the electric field to the structure of the drainage net and effectively remove the biofilm.

In particular, the present invention provides the structure of the drainage net capable of supplying the electric field without spatial or temporal restriction. Therefore, it is possible to suppress the biofilm formation in the drainage net in daily life.

Further, the present invention may provide various structures and arrangements of the electrodes that may increase electric field density, which makes it possible to apply the electric field with high efficiency to the structure of the drainage net. The effects according to the present invention are not limited to the above-mentioned effects, and more various effects are included in the present specification.

DESCRIPTION OF SPECIFIC EMBODIMENTS

Figure 1:
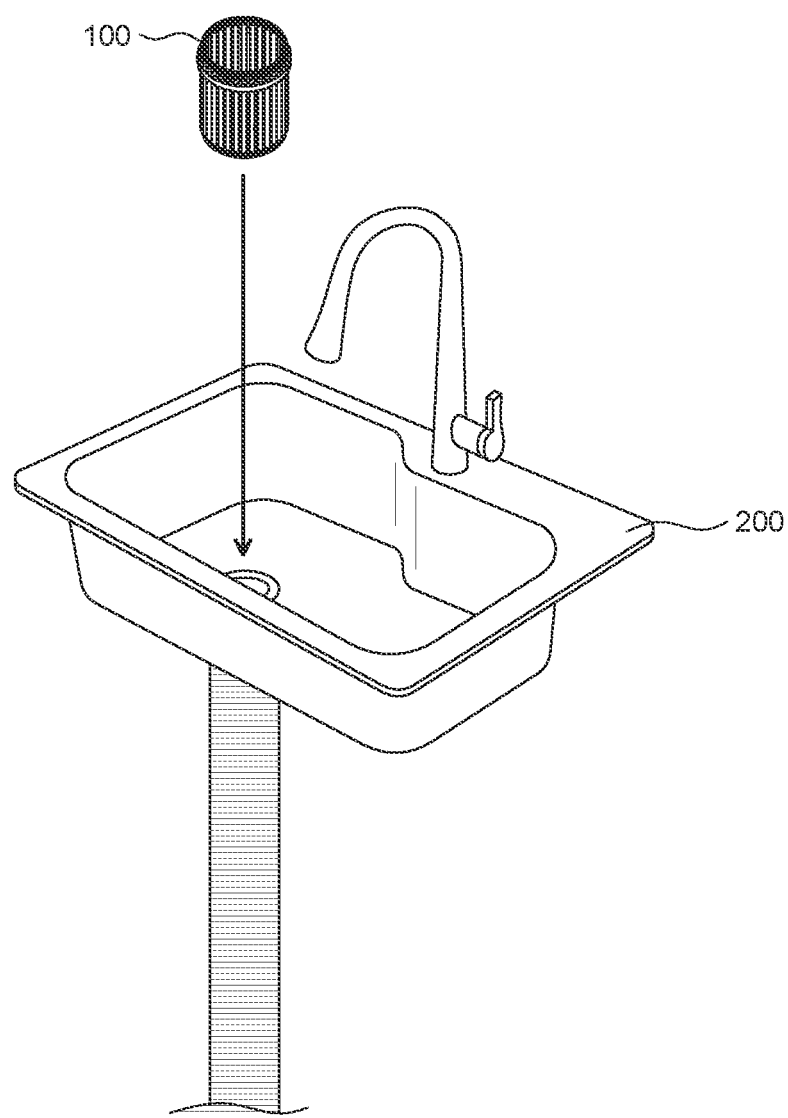
FIG. 1 is a view exemplarily illustrating a configuration of a system for suppressing biofilm formation based on a drainage net for suppressing biofilm formation according to an embodiment of the present invention.

Advantages of the present invention and methods of achieving the advantages will be clear with reference to embodiments described in detail below together with the accompanying drawings. However, the present invention is not limited to the embodiments disclosed herein but will be implemented in various forms. The embodiments of the present invention are provided so that the present invention is completely disclosed, and a person with ordinary skill in the art to which the present invention pertains can fully understand the scope of the present invention. the present invention will be defined only by the scope of the appended claims.

Shapes, sizes, ratios, angles, numbers, and the like illustrated in the drawings for explaining the embodiments of the present invention are just exemplarily illustrated, and the present invention is not limited to the contents illustrated in the drawings. In addition, in the description of the present invention, the specific descriptions of publicly known related technologies will be omitted when it is determined that the specific descriptions may unnecessarily obscure the subject matter of the present invention. The terms "comprise," "have," or "include" used in the present specification may mean that other constituent elements can be added unless these terms are used with the term "only". Unless otherwise particularly and clearly stated, the singular expressions used herein are intended to include the plural expressions.

Unless otherwise separately and explicitly stated, analyses of constituent elements are interpreted as including error ranges.

Respective features of several exemplary embodiments of the present invention may be partially or entirely coupled to or combined with each other, and as sufficiently appreciated by those skilled in the art, various technical cooperation and operations may be made, and the respective exemplary embodiments may be carried out independently of each other or carried out together correlatively.

The terms used in the present specification are defined as follows to clearly describe the present specification.

The term "drainage net main body" used in the specification of the present application refers to a strainer device inserted into a kitchen sink or a bathroom sink and configured to filter out leftover food and allow water to flow therethrough. First and second electrodes may be disposed on the drainage net main body.

In this case, the main body may be made of, but not limited to, polypropylene. The main body may be made of various types of plastic.

Meanwhile, according to the feature of the present invention, the main body of the drainage net may have a cylindrical structure opened at an upper side thereof. For example, the main body may include an annular rim portion, and a plurality of columns disposed along a periphery of the rim portion, provided inside or outside the rim portion, and configured to define a lateral side of the main body. In this case, the main body may include drainage holes defined by the plurality of columns disposed at the lateral side of the main body.

According to another feature of the present invention, the main body may further include, but not limited to, a bottom portion in which the drainage holes are formed.

The term "bottom portion" used in the specification of the present application may mean a structure disposed at a lower side of the main body and including the drainage holes to drain water. In this case, the bottom portion may be integrated with the drainage net main body. Alternatively, the bottom portion may be attached to or detached from the main body, and the bottom portion may be seated on a lower side of the main body through the opened upper side of the main body.

The terms "first electrode" and "second electrode" used in the specification of the present application mean conductive electrodes having electrical conductivity.

In this case, the first electrode and the second electrodes may each be made of at least one metal of Au, Ni, Cu, Zn, Fe, Al, Ti, Pt, Hg, Ag, Pb, and an alloy thereof. Further, the electrode may be made of at least one organic material of carbon black, carbon graphite, graphene, fullerene, and carbide.

However, the present invention is not limited thereto, and the first electrode and the second electrodes may each be an electric conductor plated with aluminum alloy or plastic chromium, or an electric conductor made of conductive silicone or conductive polymer.

In this case, the first electrode may mean an electrode having positive electric charges, and the second electrode may mean a grounded electrode. However, the present invention is not limited thereto.

According to the feature of the present invention, the first electrode and the second electrodes may be disposed on the main body of the drainage net and spaced apart from each other at a predetermined interval.

In this case, the "predetermined interval" may be 0.01 to 50 mm. More specifically, in a case in which the first electrode and the second electrodes are disposed on the main body and spaced apart from each other at an interval of 0.01 to 50 mm, a stable voltage of 0.82 V or less may be generated, and an electric field of 1.25 V/Cm or less may be applied to the structure of the drainage net. Meanwhile, in a case in which the first electrode and the second electrodes are disposed on the main body and spaced apart from each other at an interval of 20 mm or more, a voltage higher than 0.82 V may be required, and an electric field higher than 1.25 V/Cm may be applied to the structure of the drainage net.

For example, an interval between the first electrode and the second electrodes may be 0.01 to 50 mm in a state in which the first electrode is inserted into the columns disposed along the lateral side of the main body and each having an opened upper side and the second electrode is inserted into the columns disposed along the lateral side of the main body and each having an opened lower side.

With this structural feature, a voltage of 0.25 to 5 V may be applied to the drainage net main body.

According to another feature of the present invention, the first electrode and the second electrodes may each have a diameter of 0.01 to 20 mm. However, the present invention is not limited to the diameter, and the diameter of each of the two electrodes may be more variously selected depending on the material of each of the two electrodes.

Meanwhile, a height of each of the first electrode and the second electrodes may be variously set depending on a height of the main body, particularly, depending on a position of a biofilm formation point at which the biofilm is formed. For example, an electric field may be applied to a target point when a distance from each of the first electrode and the second electrodes to the biofilm formation point (target point) in the drainage net main body is 15 mm or less, particularly, 5 mm or less.

According to still another feature of the present invention, the first electrode and the second electrodes may include a plurality of circular electrodes provided on the lateral and lower sides of the main body and alternately disposed in a direction parallel to the lower side of the main body.

The term "circular electrode" used in the specification of the present application may mean an electrode shaped to surround the lateral and lower sides of the main body having the cylindrical structure.

More specifically, the first electrode may include a plurality of first circular electrodes disposed in a row at the lateral side of the main body and having the same diameter, and a plurality of second circular electrodes disposed at the lower side of the main body and having different diameters.

Further, the second electrode may include a plurality of third circular electrodes disposed in a row at the lateral side and having the same diameter, and a plurality of fourth circular electrodes disposed at the lower side and having different diameters.

In this case, the first and third circular electrodes are alternately arranged at the lateral side of the main body, and the second and fourth circular electrodes are alternately arranged at the lower side of the main body, such that the electric field may be applied to the entire region of the main body.

According to the feature of the present invention, the first circular electrode, the second circular electrode, the third circular electrode, and the fourth circular electrode may be disposed inside or outside the drainage net main body by being printed or coated. However, the present invention is not limited thereto.

Meanwhile, the shapes of the first electrode and the second electrodes are not limited to the above-mentioned shapes.

According to another feature of the present invention, the first electrode and the second electrodes may be first and second electrodes each provided in the form of a lattice pattern that surrounds a part of the lateral side of the drainage net having the cylindrical structure.

In this case, the first electrode and the second electrodes may define the lattice pattern by being spaced apart from each other at a predetermined interval.

Meanwhile, an insulating layer may be formed on an outer portion of each of the first electrode and the second electrodes.

The term "insulating layer" used in the specification of the present application may mean an intermediate insulator of a coating layer formed on a surface of the first or second electrode.

For example, the insulating layer may be made of, but not limited to, at least one of $Al_2O_3$, $SiO_2$, $Si_3N_4$, silicone, Teflon, and plastic.

The term "voltage supply unit" used in the specification of the present application may mean a unit connected to the first electrode and the second electrodes and configured to apply the AC voltage, the DC voltage, or both the AC voltage and the DC voltage to the structure of the drainage net.

According to the feature of the present invention, the voltage supply unit may supply the first electrode and/or the second electrode with both an AC voltage having an amplitude of 0.25 V to 0.82 V with a frequency of 0.1 MHz to 100 MHz and a DC voltage of 0.0001 V to 0.82 V. However, the present invention is not limited thereto, and the voltage supply unit may apply a voltage of 0.82 V or less to the first electrode and/or the second electrode.

According to another feature of the present invention, the voltage supply unit may control a total amount of energy to 1 nJ to 10 nJ to be provided to the structure of the drainage net by applying the AC voltage and the DC voltage. In this case, the voltage supply unit may be connected to a control unit configured to control the voltage to be provided to the structure of the drainage net or the first electrode and the second electrodes.

Meanwhile, the voltage supply unit may be configured as an integrated circuit configured to receive electrical energy from an external power supply source by magnetic resonance. Alternatively, the voltage supply unit may be a wireless battery including a battery cell configured as a nickel-cadmium battery, a nickel-hydrogen battery, a lithium-ion battery, or a lithium-ion polymer battery.

As a result, the first or second electrode may form an electric field on the drainage net main body on the basis of the voltage applied by the voltage supply unit. The magnetic field may destroy the structure of the biofilm previously formed on the drainage net main body and suppress the formation of a new biofilm.

Hereinafter, a system for suppressing biofilm formation based on a drainage net for suppressing biofilm formation according to the embodiment of the present invention will be specifically described with reference to FIG. 1. FIG. 1 is a view exemplarily illustrating a configuration of a system for suppressing biofilm formation based on a drainage net for suppressing biofilm formation according to an embodiment of the present invention.

Referring to a system 1000 for suppressing biofilm formation illustrated in FIG. 1, a drainage net 100 for suppressing biofilm formation according to the embodiment of the present invention may be inserted into a drainage port connected to a drainage pipe in the sink 200. In this case, an electric field formed on the drainage net 100 for suppressing biofilm formation may suppress biofilm formation in the drainage net main body or destroy and remove the structure of the previously formed biofilm.

More specifically, the drainage net 100 for suppressing biofilm formation according to the embodiment of the present invention has a structure in which a voltage supply unit configured to supply an AC voltage, a DC voltage, or both the AC voltage and the DC voltage and first and second electrodes connected to the voltage supply unit are disposed on a main body of the drainage net 100. In this case, by the electric field formed in a region of the main body, the electric field may be applied to the biofilm formed on the main body of the drainage net 100 without direct contact between the first electrode and the second electrodes, such that the structure of the biofilm may be destroyed. In particular, in a case in which a small amount of chemical agent is applied onto the drainage net 100 for suppressing biofilm formation according to the embodiment of the present invention, the molecular motion of the chemical agent may be activated by the electric field, and the permeation of chemicals into the biofilm may be facilitated, thereby effectively removing the biofilm.

Hereinafter, a structure of the drainage net for suppressing biofilm formation according to the embodiment of the present invention will be described with reference to FIGS. 2A to 2D. FIGS. 2A to 2D are views exemplarily illustrating the drainage net for suppressing biofilm formation and components thereof according to the embodiment of the present invention.

Figure 2A:
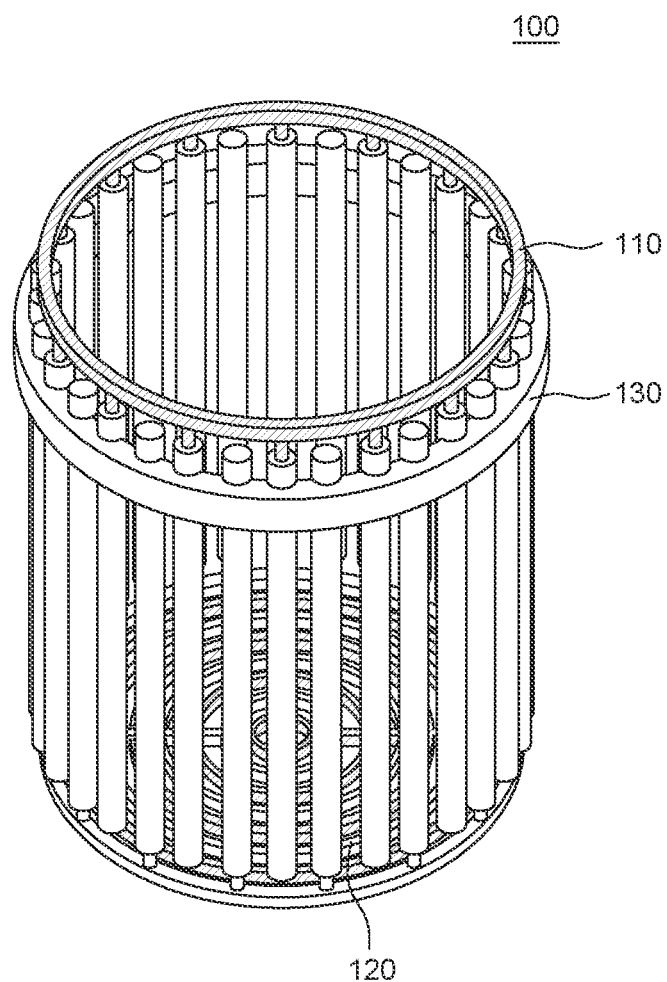
FIGS. 2A to 2D are views exemplarily illustrating the drainage net for suppressing biofilm formation and components thereof according to the embodiment of the present invention.
Figure 2B:
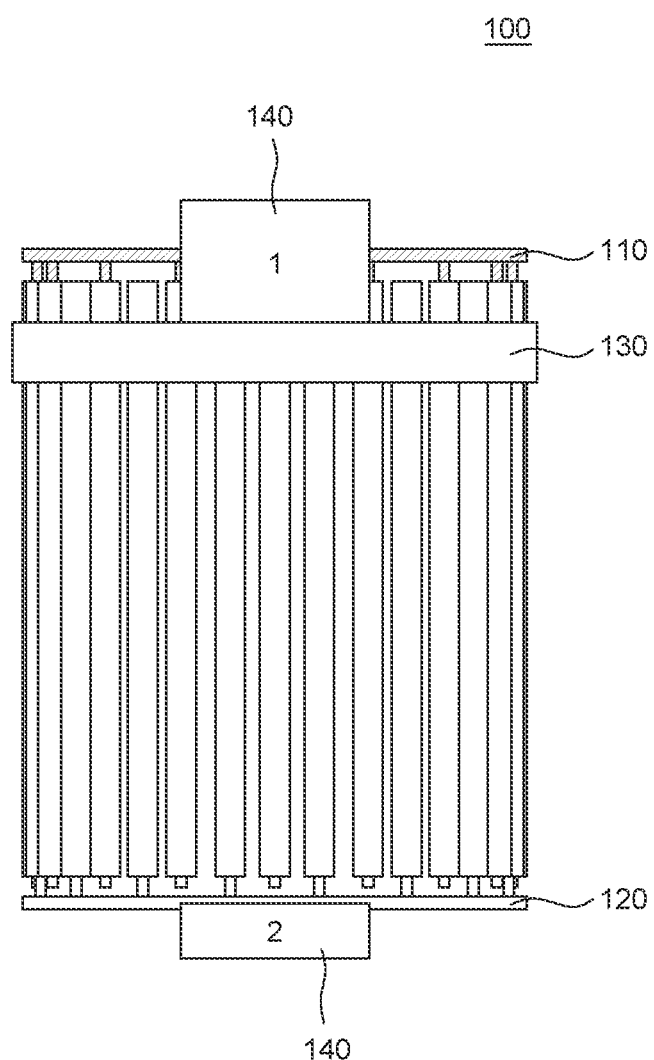

First, referring to FIGS. 2A and 2B, the drainage net 100 for suppressing biofilm formation broadly includes a first electrode 110 having positive electric charges and inserted into a drainage net main body 130, a second electrode 120 grounded and inserted into the drainage net main body 130 in a direction opposite to a direction in which the first electrode 110 is inserted, and a voltage supply unit 140 configured to supply a voltage to the first electrode 110. In this case, the voltage supply unit 140 may be disposed at an upper or lower side of the drainage net 100 for suppressing biofilm formation, but the present invention is not limited thereto. Meanwhile, a control unit (not illustrated) configured to control the voltage of the voltage supply unit 140 may further be disposed on the drainage net 100 for suppressing biofilm formation. For example, the control unit may control a total amount of energy to 1 nJ to 10 nJ to be provided to the main body 130 by the application of the AC voltage and the DC voltage by the voltage supply unit 140.

Meanwhile, the main body 130 of the drainage net 100 for suppressing biofilm formation may have a structure opened at upper and lower sides thereof.

Figure 2C:
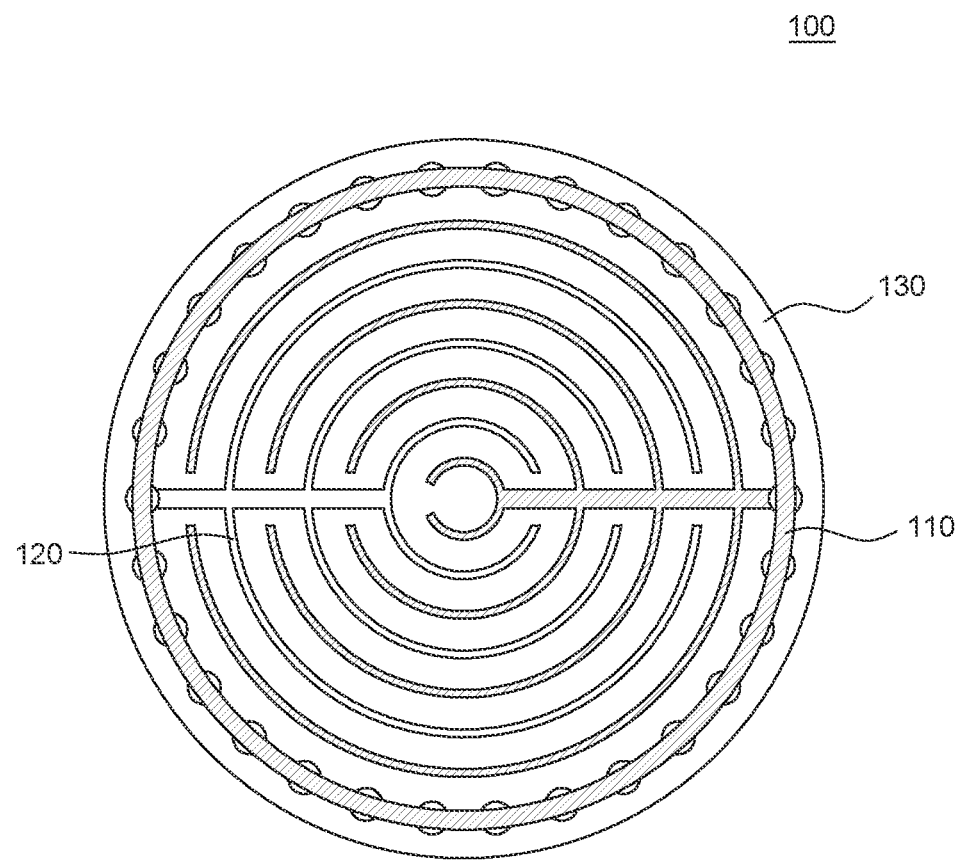

In this case, referring to the top plan view in FIG. 2C related to the drainage net 100 for suppressing biofilm formation, the first electrode 110 may include a plurality of circularly structured electrodes having different diameters and disposed at predetermined intervals, the second electrode 120 may include a plurality of circularly structured electrodes having different diameters and disposed to be spaced apart from the first electrode 110 at a predetermined interval, and the lower side of the drainage net 100 for suppressing biofilm formation may be formed as the first electrode and the second electrodes 110 and 120 are inserted into the main body 130.

Figure 2D:
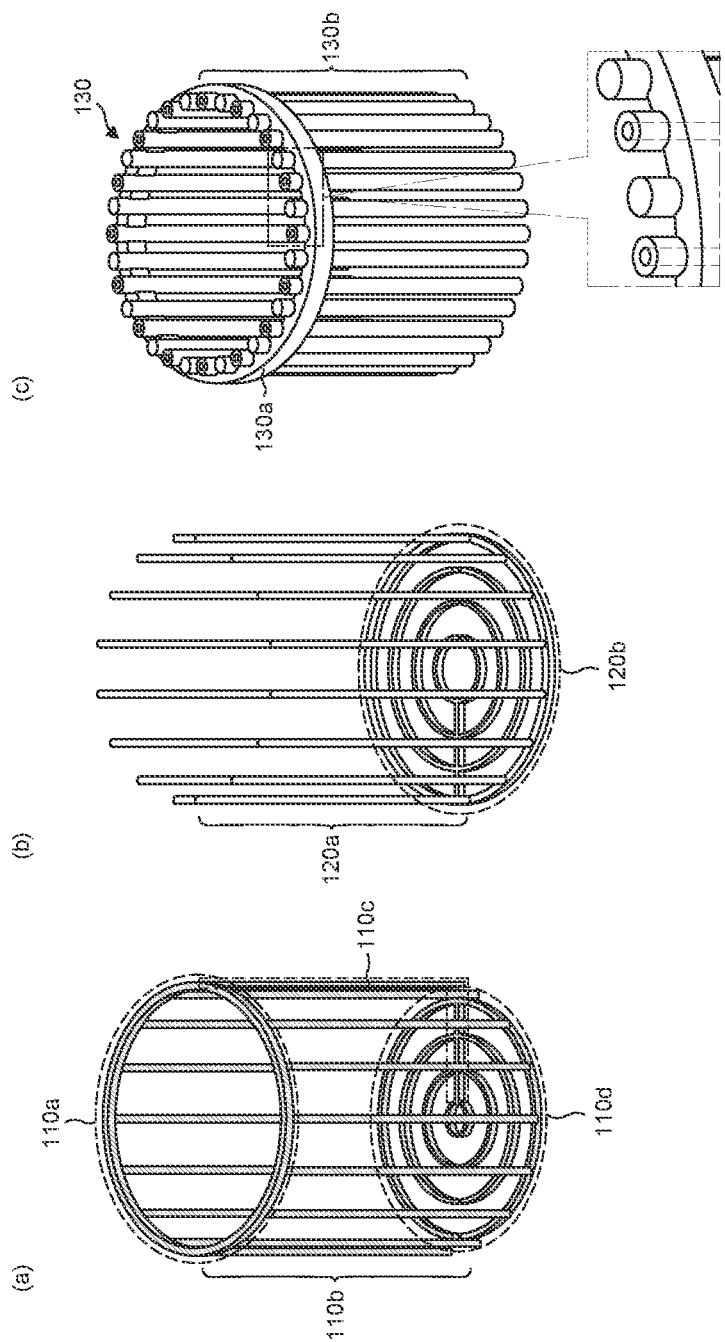

More specifically, referring to FIG. 2D (a), the first electrode 110 may include: an annular electrode 110a corresponding to a rim of the main body 130 when the annular electrode 110a is inserted into the main body 130; first insertion electrodes 110b disposed along a periphery of the annular electrode 110a, each having a predetermined height, and fastened to the main body 130; a support electrode 110c extending from the annular electrode 110a; and bottom electrodes 110d fixed to the support electrode 110c. In this case, the support electrode 110c may be formed inside the first insertion electrode 110b. Further, a diameter of the bottom electrode 110d may be smaller than a diameter of the annular electrode 110a and a diameter of the lower side of the main body 130. Therefore, when the first electrode 110 is inserted into the main body 130, the bottom electrodes 110d may be disposed at the lower side of the main body 130. Meanwhile, the first electrode 110 may be an integrated electrode made by connecting the annular electrode 110a, the first insertion electrodes 110b, the support electrode 110c, and the bottom electrodes 110d, but the present invention is not limited thereto. For example, the first electrode 110 includes two electrodes including one electrode made by connecting the annular electrode 110a and the first insertion electrodes 110b, and the other electrode made by connecting the support electrode 110c and the bottom electrodes 110d.

Referring to FIG. 2D (b), the second electrode 120 may include: second insertion electrodes 120a capable of being fastened to the main body 130 and each having a predetermined height; and base electrodes 120b disposed at one end of the second insertion electrodes 120a and disposed at the lower side of the main body 130 when the base electrodes 120b are inserted into the main body 130. In this case, a diameter of the base electrode 120b may be larger than a diameter of the bottom electrode 110d of the first electrode 110 and equal to an outer diameter of the lower side of the main body 130, but the present invention is not limited thereto. Meanwhile, when the first electrode and the second electrodes 110 and 120 are inserted into the main body 130, the base electrodes 120b and the bottom electrodes 110d may alternately disposed at predetermined intervals at the lower side of the main body 130. In this case, the interval between the base electrode 120b and the bottom electrode 110d may be, but not limited to, 0.01 to 50 mm.

Referring further to FIG. 2D (c), the main body 130 may include an annular rim portion 130a, and a plurality of columns 130b disposed along a periphery of the rim portion 130a, provided inside the rim portion 130a, and each having a predetermined height. That is, the main body 130 may include drainage holes defined by the plurality of columns 130b. In this case, a position of the rim portion 130b may be variously selected as long as the plurality of columns 130b is fixed to the rim portion 130b. Meanwhile, an interval between the plurality of columns 130b may be, but not limited to, 0.01 to 50 mm. According to the feature of the present invention, the plurality of columns 130b includes: columns each opened at an upper side thereof and having an inner diameter such that the first insertion electrodes 110b of the first electrode 110 are inserted into the columns; and columns each opened at a lower side thereof and having an inner diameter such that the second insertion electrodes 120a of the second electrode 120 are inserted into the columns. In this case, the inner diameter of each of the plurality of columns 130b may be equal to or larger than the diameter of the first insertion electrode 110b and the diameter of the second insertion electrode 120a. According to another feature of the present invention, the columns each having the opened lower side and the columns each having the opened upper side may be alternately disposed along the rim portion 130a. In this case, the plurality of columns 130b may have various shapes, such as a shape opened at both the upper and lower sides thereof, as long as the first and second insertion electrodes 110b and 120a are inserted into the columns.

Meanwhile, the main body 130 has a cylindrical structure opened at both the upper and lower sides thereof. However, when the first electrode and the second electrodes 110 and 120 are fastened to the main body 130, the main body 130 may have the lower side having the drainage holes defined by the arrangements of the bottom electrodes 110d and the base electrodes 120b. In this case, the heights of the first and second insertion electrodes 110b and 120a may be variously set depending on a height at a target point at which the magnetic field is applied, i.e., a height at a point at which the biofilm formation is predicted. For example, a distance between the first and second insertion electrodes 110b and 120a and the point (target point) at which the biofilm formation is predicted may be set to 15 mm or less, particularly, 5 mm or less. With this structural feature, the electric field formed by the two electrodes may be applied to the target point.

The drainage net for suppressing biofilm formation according to the embodiment may provide the effect of suppressing the biofilm formation by applying the electric field with high efficiency to the main body of the drainage net by using the above-mentioned structural feature.

Figure 3A:
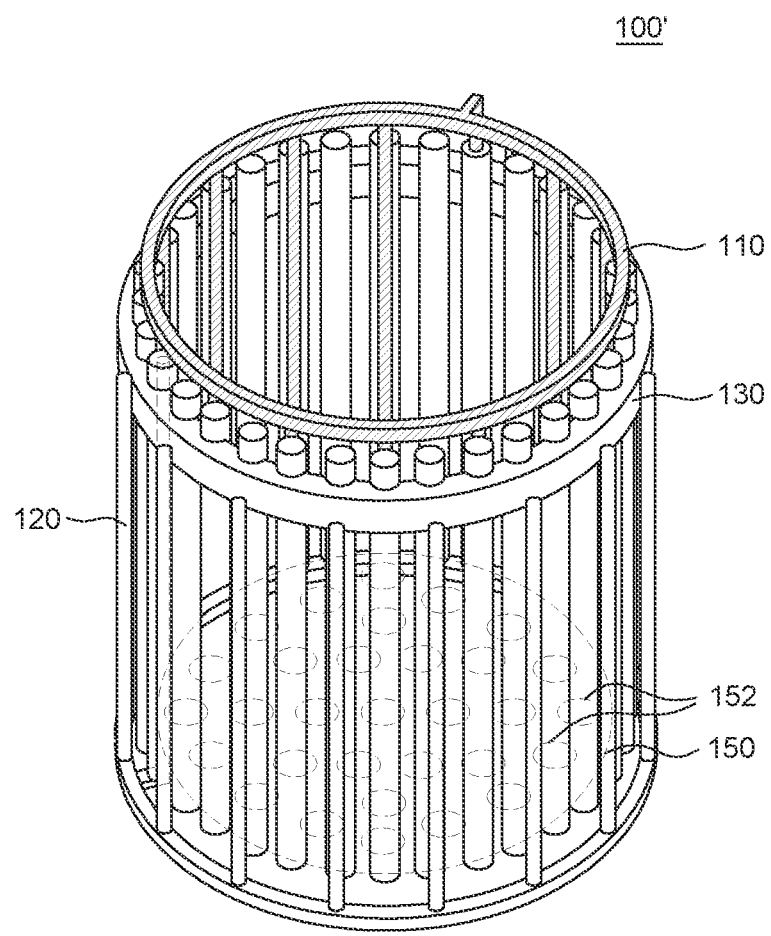
FIGS. 3A to 3C are views exemplarily illustrating a configuration of a drainage net for suppressing biofilm formation according to another embodiment of the present invention.
Figure 3B:
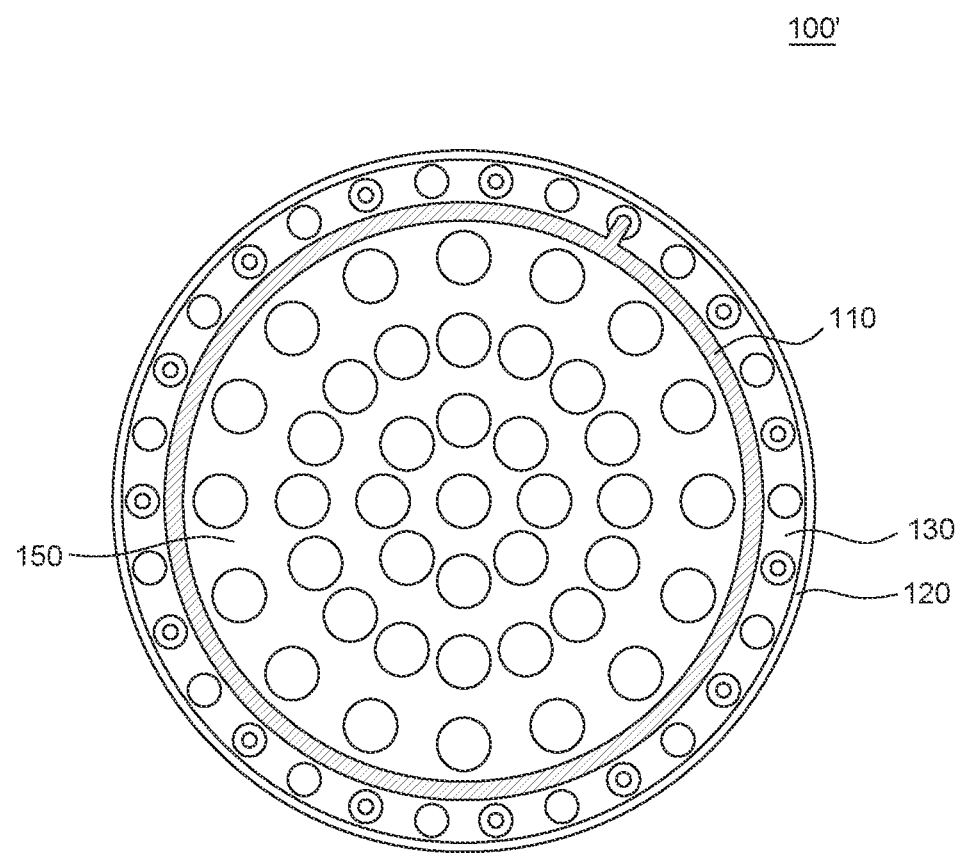
Figure 3C:
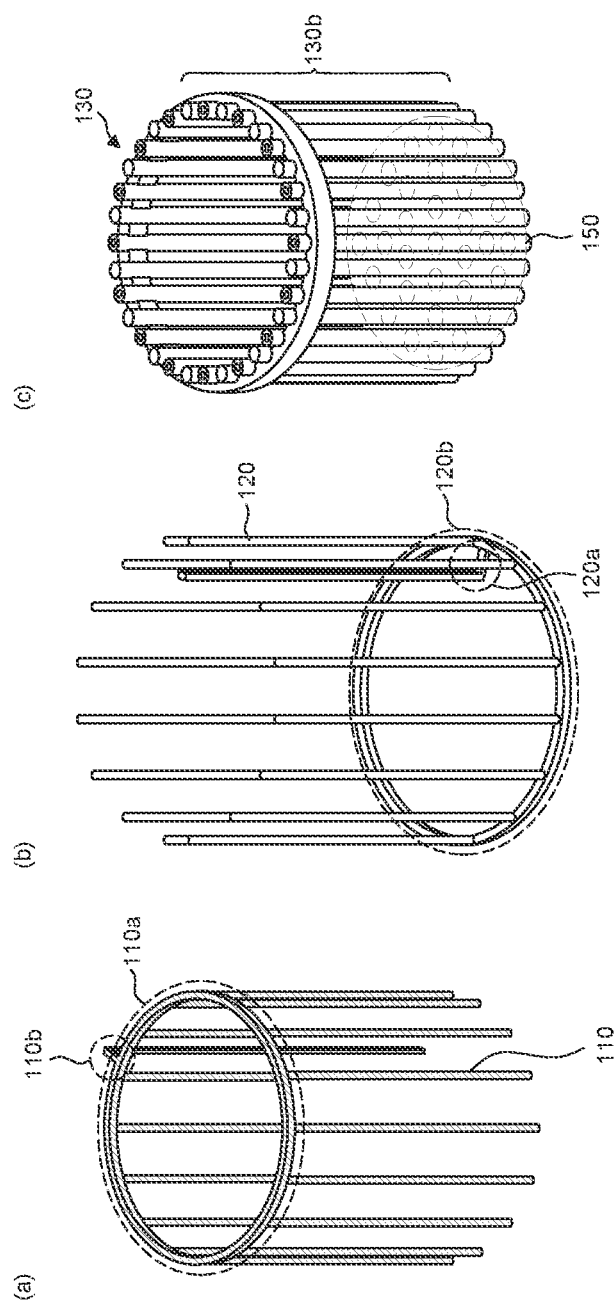

Hereinafter, a structure of a drainage net for suppressing biofilm formation according to another embodiment of the present invention will be described with reference to FIGS. 3A to 3C. FIGS. 3A to 3C are views exemplarily illustrating a configuration of a drainage net for suppressing biofilm formation according to another embodiment of the present invention.

First, referring to the front view in FIG. 3A related to a drainage net 100' for suppressing biofilm formation and a top plan view in FIG. 3B related to the drainage net 100' for suppressing biofilm formation, the drainage net 100' for suppressing biofilm formation according to another embodiment of the present invention may broadly include: a first electrode 110 having positive electric charges and inserted into an inner side of the drainage net main body 130; and a second electrode 120 grounded and inserted into an outer side of the drainage net main body 130. Further, the drainage net 100' for suppressing biofilm formation may further include a bottom portion 150 seated at the lower side of the main body 130 and configured to prevent leftover food from being discharged. In this case, a plurality of drainage holes 152 may be formed in the bottom portion 150.

More specifically, referring to FIG. 3C (a) and (c), the first electrode 110 may include: an annular electrode 110a corresponding to the rim of the main body 130, and first insertion electrodes 110b disposed along a periphery of the annular electrode 110a, each having a predetermined height, and inserted into the inner side of the main body 130. In this case, a diameter of the annular electrode 110a may be equal to or smaller than an inner diameter of the upper side of the main body 130. Further, at least one of the first insertion electrodes 110b may be disposed outside the annular electrode 110a so as to be fastened directly to a plurality of columns 130b constituting the main body 130.

Referring to FIG. 3C (b) and (c), the second electrode 120 may include: second insertion electrodes 120a inserted into the outer side of the main body 130 and each having a predetermined height; and a base electrode 120b disposed at one end of the second insertion electrodes 120a and configured to correspond to the bottom portion 150 of the main body 130 when the base electrode 120b is inserted into the main body 130. In this case, a diameter of the base electrode 120b may be larger than a diameter of the lower side of the main body 130, i.e., an inner diameter of the bottom portion 150. Further, at least one of the second insertion electrodes 120a may be disposed inside the base electrode 120b so as to be fastened directly to the plurality of columns 130b constituting the main body 130.

In this case, an interval between the first and second insertion electrodes 110b and 120a may be, but not limited to, 0.01 to 50 mm. With this structural feature, the first electrode and the second electrodes 110 and 120 may be more effectively fixed to the main body 130 and suppress the biofilm formation by applying the magnetic field to the entire region of the main body 130.

That is, the drainage net for suppressing biofilm formation according to another embodiment may provide the effect of suppressing the biofilm formation by applying the electric field with high efficiency to the main body of the drainage net by using the above-mentioned structural feature.

Hereinafter, a structure of a drainage net for suppressing biofilm formation according to still another embodiment of the present invention will be described with reference to FIGS. 4A to 4D. FIGS. 4A to 4D are views exemplarily illustrating a configuration of a drainage net for suppressing biofilm formation according to still another embodiment of the present invention.

Figure 4A:
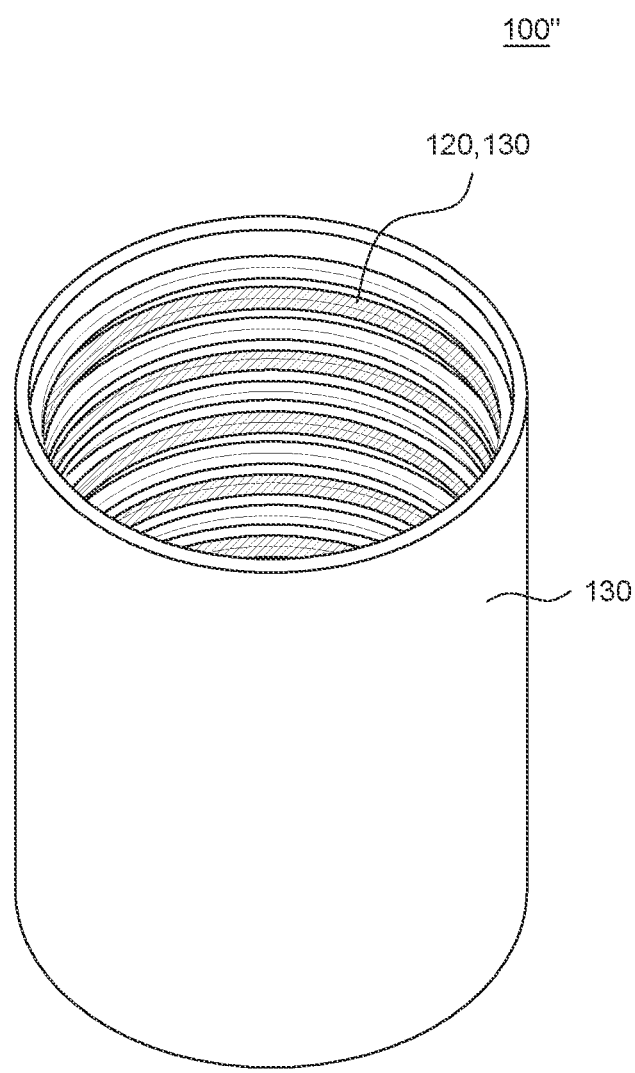
FIGS. 4A to 4D are views exemplarily illustrating a configuration of a drainage net for suppressing biofilm formation according to still another embodiment of the present invention.
Figure 4B:
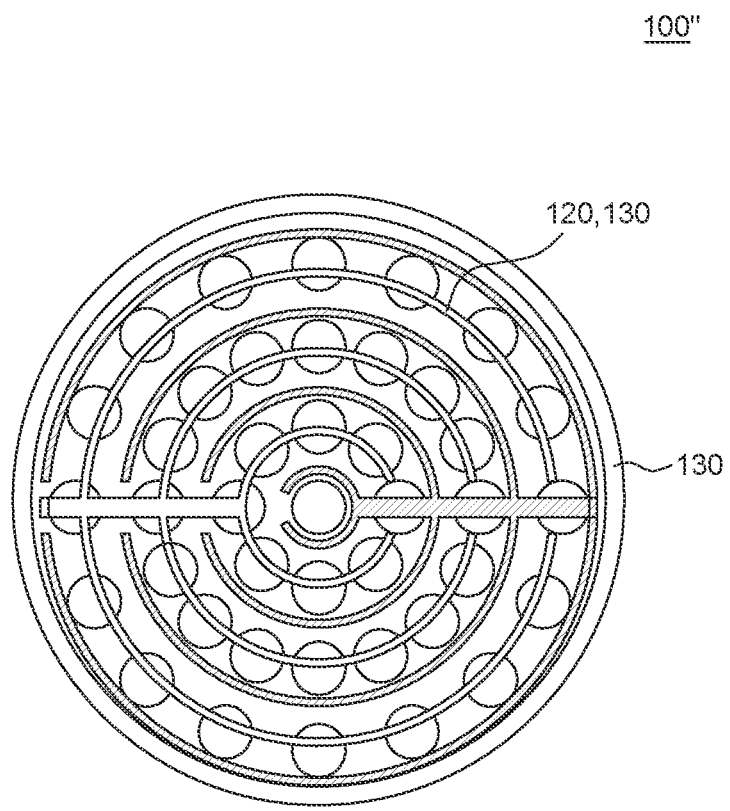

First, referring to the front view in FIG. 4A related to a drainage net 100" for suppressing biofilm formation and the top plan view in FIG. 4B related to the drainage net 100" for suppressing biofilm formation, the drainage net 100" for suppressing biofilm formation according to another embodiment of the present invention may broadly include: a main body 130 opened at an upper side thereof and having drainage holes formed at a lower side thereof; a plurality of first electrodes 110 having positive electric charges, provided at lateral and lower sides of the drainage net main body 130, and disposed in a direction parallel to the lower side; and second electrodes 120 grounded, spaced apart from the first electrodes 110 at predetermined intervals, and disposed at the lateral and lower sides of the drainage net main body 130.

Figure 4C:
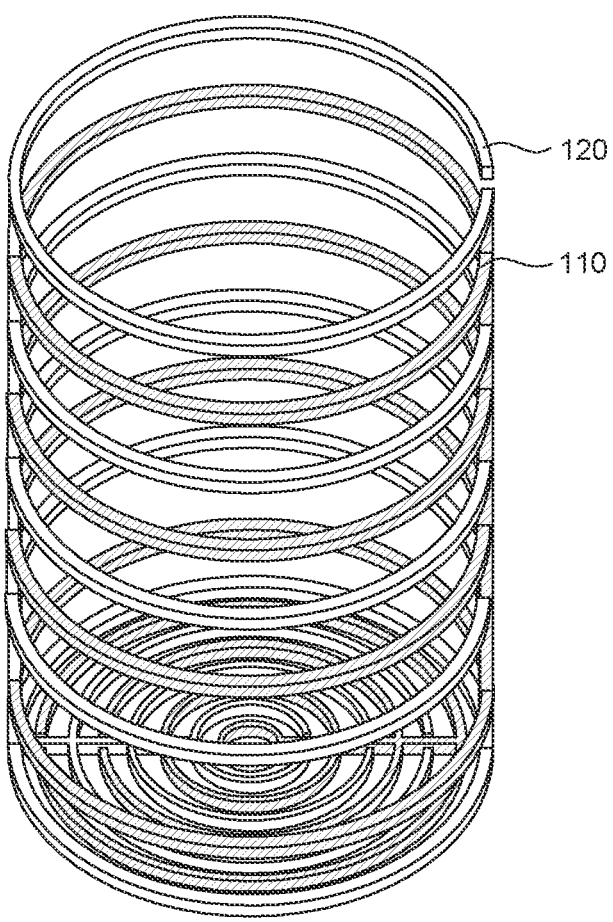

In this case, referring to FIG. 4C, the first electrode and the second electrodes 110 and 120 may each have an annular structure may be alternately disposed at the lateral and lower sides of the main body 130. According to the feature of the present invention, the first electrode and the second electrodes 110 and 120 may be printed or plated and alternately disposed inside or outside the main body 130.

Figure 4D:
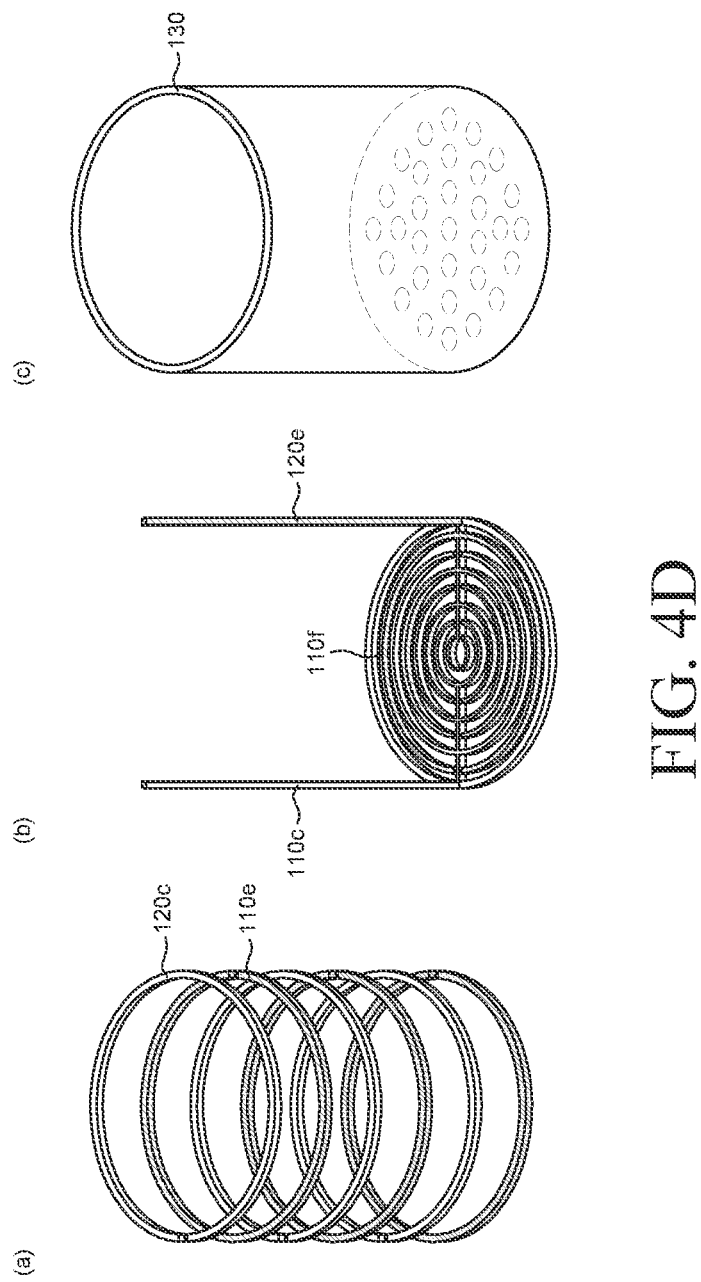

More specifically, referring to FIG. 4D (a), (b), and (c), the first electrode 110 may include first circular electrodes 110e disposed at the lateral side of the main body 130, and second circular electrodes 110f disposed at the lower side of the main body 130. Further, the second electrodes 120 may include third circular electrode 120c disposed at the lateral side of the main body 130, and fourth circular electrodes 120d disposed at the lower side of the main body 130. In this case, the first and third circular electrodes 110e and 120c may be alternately arranged at the lateral side of the main body 130, and the second and fourth circular electrodes 110f and 120d may be alternately arranged at the lower side of the main body 130. In this case, the plurality of second circular electrodes 110f and the plurality of fourth circular electrodes 120d may have different diameters and be arranged at the lower side so as to be spaced apart from one another at predetermined intervals. Meanwhile, the first electrode 110 may further include a support electrode 110c fixed to the plurality of second circular electrodes 110f disposed at the lower side of the main body 130. The support electrode 110c may be connected to the first circular electrodes 110e disposed at the lateral side of the main body 130. Further, the second electrode 120 may further include a support electrode 120e fixed to the plurality of fourth circular electrodes 120d disposed at the lower side of the main body 130. The support electrode 120e may be connected to the third circular electrodes 120c disposed at the lateral side of the main body 130. In this case, the four circular electrodes 110e, 110f, 120c, and 120d may each have a 'C' shape opened at one side thereof. Therefore, the first electrode and the second electrodes 110 and 120 each having the circular structure may be stably arranged at the lateral and lower sides of the main body 130 having the cylindrical structure, such that the voltage predetermined depending on the arrangement may be efficiently applied to the main body 130.

That is, the drainage net for suppressing biofilm formation according to still another embodiment may provide the effect of suppressing the biofilm formation by applying the electric field with high efficiency to the main body of the drainage net by using the above-mentioned structural feature.

Figure 5A:
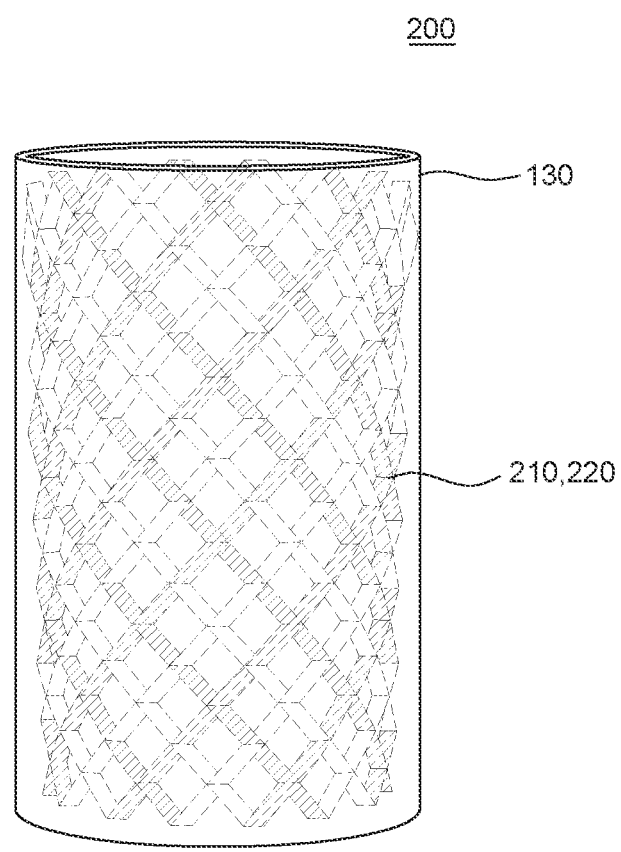
FIGS. 5A to 5C are views exemplarily illustrating a configuration of an insertable device for suppressing biofilm formation according to various embodiments of the present invention.
Figure 5B:
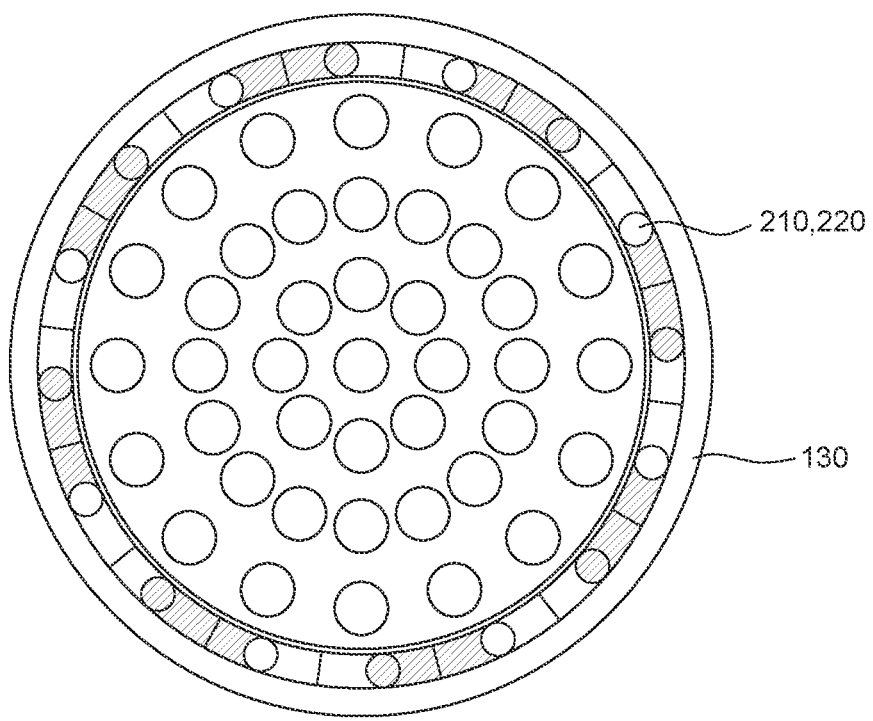
Figure 5C:
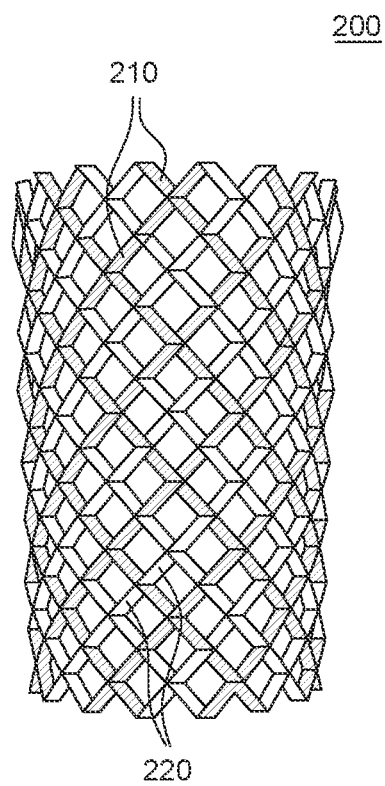

Hereinafter, a structure of an insertable device for suppressing biofilm formation according to the embodiment of the present invention will be described with reference to FIGS. 5A to 5C. FIGS. 5A to 5C are views exemplarily illustrating a configuration of an insertable device for suppressing biofilm formation according to various embodiments of the present invention.

First, referring to FIG. 5A, an insertable device 300 for suppressing biofilm formation according to the embodiment of the present invention may include first and second lattice-patterned electrodes 210 and 220 configured to surround the lateral side of the main body of the drainage net having the cylindrical structure. In this case, the first and second lattice-patterned electrodes 210 and 220 may be spaced apart from each other at a predetermined interval and define a single lattice pattern.

Referring to the front view in FIG. 5B and the top plan view in FIG. 5C, the insertable device 300 for suppressing biofilm formation including the first and second lattice-patterned electrodes 210 and 220 may have a diameter equal to or smaller than the inner diameter of the main body 130 so that the insertable device 300 may be inserted into the main body 130 of the drainage net having the cylindrical structure. However, the present invention is not limited thereto, and the insertable device 300 for suppressing biofilm formation may have a diameter equal to or larger than an outer diameter of the main body 130 so that the insertable device 300 surrounds an outer portion of the main body 130 of the drainage net having the cylindrical structure.

The insertable device 300 for suppressing biofilm formation, which is easily attached or detached as described above, may apply the electric field to the main body 130, thereby suppressing the biofilm formation or facilitating the process of destroying and removing the structure of the previously formed biofilm.

Meanwhile, the contact surfaces between the first and second lattice-patterned electrodes 210 and 220 or the entire regions of the first and second lattice-patterned electrodes 210 and 220 may be coated with insulating layers (not illustrated) to prevent overloads caused by the generation of the voltage. Therefore, the first and second lattice-patterned electrodes 210 and 220 may stably apply the electric field to the main body 130 of the drainage net. According to the feature of the present invention, the insulating layer may be made of, but not limited to, at least one of $Al_2O_3$, $SiO_2$, $Si_3N_4$, silicone, Teflon, and plastic. Further, the insulating layer may cover a part of the voltage supply unit (not illustrated) connected to the first and second lattice-patterned electrodes 210 and 220.

The insertable device for suppressing biofilm formation according to the embodiment may provide the effect of suppressing the biofilm formation by applying the electric field with high efficiency to the structure of the drainage net by using the above-mentioned structural feature.

Although the embodiments of the present invention have been described in detail with reference to the accompanying drawings, the present invention is not limited thereto and may be embodied in many different forms without departing from the technical concept of the present invention. Therefore, the embodiments disclosed in the present invention are provided for illustrative purposes only but not intended to limit the technical concept of the present invention. The scope of the technical spirit of the present invention is not limited thereby. Therefore, it should be understood that the above-described exemplary embodiments are illustrative in all aspects and do not limit the present specification. The protective scope of the present invention should be construed based on the following claims, and all the technical spirit in the equivalent scope thereto should be construed as falling within the scope of the present invention.

DESCRIPTION OF REFERENCE NUMERALS 100, 100', 100": Drainage net for suppressing biofilm formation
110: First electrode
110a: Annular electrode
110b: First insertion electrode
110c, 120e: Support electrode
110d: Bottom electrode
110e: First circular electrode
110f: Second circular electrode
120: Second electrode
120a: Second insertion electrode
120b: Base electrode
120c: Third circular electrode
120d: Fourth circular electrode
130: Main body
130a: Rim portion
130b: Plurality of columns
132: Attachment/detachment unit
140: Voltage supply unit
150: Bottom portion
152: Drainage hole
200: Sink
300: Insertable device for suppressing biofilm formation
210: First lattice-patterned electrode
220: Second lattice-patterned electrode
1000: System for suppressing biofilm formation

What is claimed is:

1. A drainage net for suppressing biofilm formation, the drainage net comprising:
a drainage net main body having a cylindrical structure opened at an upper side thereof and having drainage holes;
a first electrode disposed outside or inside the main body;
a second electrode grounded, spaced apart from the first electrode at a predetermined interval, and disposed outside or inside the main body; and
a voltage supply unit configured to apply, to the first electrode, at least one of an alternating current (AC) voltage, a direct current (DC) voltage, and a voltage in which the AC voltage and the DC voltage are superimposed.

2. The drainage net of claim 1,
wherein the main body comprises:
an annular rim portion; and
a plurality of columns disposed along the rim portion and provided inside or outside the rim portion,
wherein the plurality of columns is each opened at an upper or lower side thereof, and the drainage holes are formed between the plurality of columns,
wherein the first electrode comprises:
a first insertion electrode insertable into the opened upper or lower side; and
an annular electrode disposed one side of the first insertion electrode and corresponding to the rim portion, and wherein the second electrode comprises:
a second insertion electrode insertable into the remaining opened upper or lower side; and
a base electrode disposed at the lower side when the second insertion electrode is inserted into the remaining opened upper or lower side and comprising a plurality of circular electrodes having different diameters and disposed to be spaced apart from one another.

3. The drainage net of claim 2, wherein the main body is that the columns each opened only at the upper side thereof among the plurality of columns and the columns each opened only at the lower side thereof among the plurality of columns are alternately arranged inside or outside the rim portion of the main body.

4. The drainage net of claim 2, wherein the first electrode further comprises:
a support electrode disposed in parallel with the first insertion electrode; and
a bottom electrode perpendicularly connected to one end of the support electrode and spaced apart from the base electrode of the second electrode at a predetermined interval when the first insertion electrode is inserted into the opened upper or lower side.

5. The drainage net of claim 2, wherein the main body further comprises a bottom portion having a plurality of drainage holes, the bottom portion being fixed to or seated on the lower side of the main body.

6. The drainage net of claim 2,
wherein the first electrode is disposed at a portion inside or outside the main body, and
wherein the second electrode is disposed at the remaining portion inside or outside the main body.

7. The drainage net of claim 2, wherein the first insertion electrode is provided in plural, the second insertion electrode is provided in plural, and at least one of the plurality of first insertion electrodes and at least one of the plurality of second insertion electrode are insertable into the opened upper or lower sides.

8. The drainage net of claim 1, wherein at least one of the AC voltage, the DC voltage, and the voltage in which the AC voltage and the DC voltage are superimposed, which is 0.25 to 5 V, is applied to a surface of the drainage net.

9. The drainage net of claim 1, wherein the predetermined interval is 0.01 to 50 mm, and a diameter of the first electrode or the second electrode is 0.01 to 20 mm.

10. A drainage net for suppressing biofilm formation, the drainage net comprising:
a main body having a cylindrical structure having lateral and lower sides;
a plurality of first electrodes disposed on the lateral and lower sides and provided in a direction parallel to the lower side;
a second electrode grounded, spaced apart from the plurality of first electrodes, disposed on the lateral and lower sides, and provided in the direction parallel to the lower side; and
a voltage supply unit configured to supply a voltage to the first electrode.

11. The drainage net of claim 10,
wherein the first electrode comprises:
a plurality of first circular electrodes disposed in a row at the lateral side and having the same diameter; and
a plurality of second circular electrodes disposed at the lower side and having different diameters,
wherein the second electrode comprises:
a plurality of third circular electrodes disposed in a row at the lateral side and having the same diameter; and
a plurality of fourth circular electrodes disposed at the lower side and having different diameters, and
wherein the main body is that the first and third circular electrodes are alternately arranged at the lateral side of the main body, and the second and fourth circular electrodes are alternately arranged at the lower side of the main body.

12. An insertable device for suppressing biofilm formation, the insertable device comprising:
a first electrode configured to define a lattice pattern configured to surround a part of a lateral side of a drainage net having a cylindrical structure;
a second electrode grounded, spaced apart from the first electrode, and configured to define the lattice pattern together with the first electrode to surround a part of the lateral side of the drainage net; and
a voltage supply unit configured to supply a voltage to the first electrode.

13. The insertable device of claim 12, further comprising:
an insulating layer configured to surround at least a part of the first electrode or the second electrode,
wherein the insulating layer is made of at least one of $Al_2O_3$, $SiO_2$, $Si_3N_4$, silicone, Teflon, and plastic.

* * * * *